United States Patent [19]

Friauf et al.

[11] 4,395,635
[45] Jul. 26, 1983

[54] GAMMA RAY COINCIDENCE ANALYSIS SYSTEM

[75] Inventors: Walter S. Friauf; Rodney A. Brooks, both of Bethesda; Victor J. Sank, Wheaton; Horace E. Cascio, Olney, all of Md.

[73] Assignee: The United States of America as represented by the Department of Health and Human Services, Washington, D.C.

[21] Appl. No.: 228,681

[22] Filed: Jan. 26, 1981

[51] Int. Cl.³ ............................................. G01T 1/20
[52] U.S. Cl. ..................................... 250/366; 250/369
[58] Field of Search ..................... 250/363 S, 366, 369

[56] References Cited

U.S. PATENT DOCUMENTS

| | | | |
|---|---|---|---|
| 3,772,512 | 11/1973 | Lanez | 250/366 |
| 4,031,392 | 6/1977 | Girand et al. | 250/369 |
| 4,181,855 | 1/1980 | Horrocks | 250/366 |
| 4,217,497 | 8/1980 | Daniels | 250/369 |
| 4,284,890 | 8/1981 | Thompson | 250/366 |

Primary Examiner—Bruce C. Anderson
Attorney, Agent, or Firm—Browdy & Neimark

[57] ABSTRACT

A gamma ray coincidence analysis system for a multichannel nuclear imaging device of the type employing scintillation detectors in ring-like arrays, with the detectors arranged in quadrants of the rings. The scintillation detectors in a ring have output circuits including respective timing discriminators and OR gates, and respective energy discriminators providing delayed energy pulses, and wherein timing pulses from the respective quadrants are fed via the OR gates to the inputs of a four-input coincidence detector without any delay except for a small delay internal to the discriminators and the very small delay of the OR gates. The delay of the energy pulses at the energy discriminators is for an energy validation period of 500 nsec. The output pulse from the coincidence detector is subsequently delayed for a similar period for verification of the energy levels of the two channels causing the coincidence. A data output signal is generated responsive to the concurrence of the delayed coincidence signal and the delayed energy verification pulses.

12 Claims, 6 Drawing Figures

GAMMA RAY COINCIDENCE ANALYSIS SYSTEM

FIELD OF THE INVENTION

This invention relates to positron emission tomographs, and more particularly to a gamma ray coincidence analysis system for a multichannel nuclear emission tomograph of the type employing rings of scintillation detectors arranged in quadrants, with respective detectors defining scintillation detection channels.

BACKGROUND OF THE INVENTION

The prior art pertinent to the present invention is exemplified by the technique described in the publication of C. V. Thompson et al, "Positome II: A High Efficiency Positron Imaging Device for Dynamic Brain Studies", IEEE Trans. Nucl. Sci. NS.-26:583–589, 1979. In the system described in this publication, the timing pulse in each channel is delayed about 500 ns or more, until the energy of the pulse has been verified, and then it is presented to a coincidence detector. This technique has two disadvantages: Firstly, a precision delay is needed for each channel, and this becomes highly expensive in a positron emission tomograph (PET) scanner with hundreds of channels. Secondly, any instability in the channel delays directly degrades the accuracy with which time coincidence between events in different channels can be determined, and the instability will be proportional to the magnitude of the desired delay.

Further background information pertinent to the present invention is provided in the publication of R. A. Brooks et al, "Design of a High Resolution Positron Emission Tomograph: The Neuro-PET", Journal of Computer Assisted Tomography, 4(1):5–13, February, 1980, incorporated by reference.

The patent literature, for example, De Luca, U.S. Pat. No. 3,935,462; Alvarez et al, U.S. Pat. No. 4,029,963; Giraud et al, U.S. Pat. No. 4,031,392; Brunett et al, U.S. Pat. No. 4,042,811; Cox et al, U.S. Pat. No. 4,044,240; Lyons, U.S. Pat. No. 4,181,939; and Daniels et al, U.S. Pat. No. 4,217,497 show systems including computers interfaced with radiation detectors and nuclear imaging systems, but these do not solve the problems noted above.

SUMMARY OF THE INVENTION

The system of the present invention overcomes the above-mentioned two main problems. In the system of the present invention, the timing pulses from groups of channels (for the respective quadrants of scintillation detectors in the rings of detectors) are fed to a coincidence detector, without any delay except a small delay internal to the discriminators and the very small propagation delay of the OR gates employed between the discriminators and the coincidence detector. Thus, the highest possible timing accuracy is achieved. The coincidence pulse is then delayed pending verification of the energy levels of the two channels causing the coincidence. The important advantageous features of the present invention include the following:

1. Coincidence detection amongst timed pulses is provided long before the energy of the inputs that generated the timing pulses has been verified.
2. Delay of coincidence information, rather than delay of channel time information, is provided for a time sufficient to allow accurate energy verification.
3. Rejection of coincidences is obtained unless both of the pulses giving rise to the coincidence later pass the energy verification test.
4. Transmission of the detector identification information is accomplished at the time of energy verification under comparatively non-stringent timing requirements.
5. Use is made of read-only memories to control accession of the proper detector identification information.

Accordingly, a main object of the present invention is to provide an improved gamma ray coincidence analysis system for a multichannel nuclear emission tomograph which overcomes the deficiencies and disadvantages of previously employed coincidence analysis systems.

A further object of the present invention is to provide a improved multichannel nuclear emission tomograph of the type employing rings of scintillation detectors wherein the detectors are arranged in groups, such as quadrants, wherein a timing signal can be developed for each quadrant, wherein determination of detector signal coincidences between quadrants is provided, wherein quadrant pair information is encoded, wherein delay of quadrant pair information is provided pending completion of energy verification of the two channels involved in the coincidence, wherein use is made of the delayed quadrant pair information to access the energy verification signals of the two channels involved, at the proper time, wherein transmission is achieved of the detector pair information if both channels pass energy verification, and wherein use is made of read-only memories to effect the above-mentioned timely access use of the delayed energy verification signals of the two involved channels.

BRIEF DESCRIPTION OF THE DRAWINGS

Further objects and advantages of the invention will become apparent from the following description and claims, and from the accompanying drawings, wherein:

DESCRIPTION OF A PREFERRED EMBODIMENT

Figure 1:
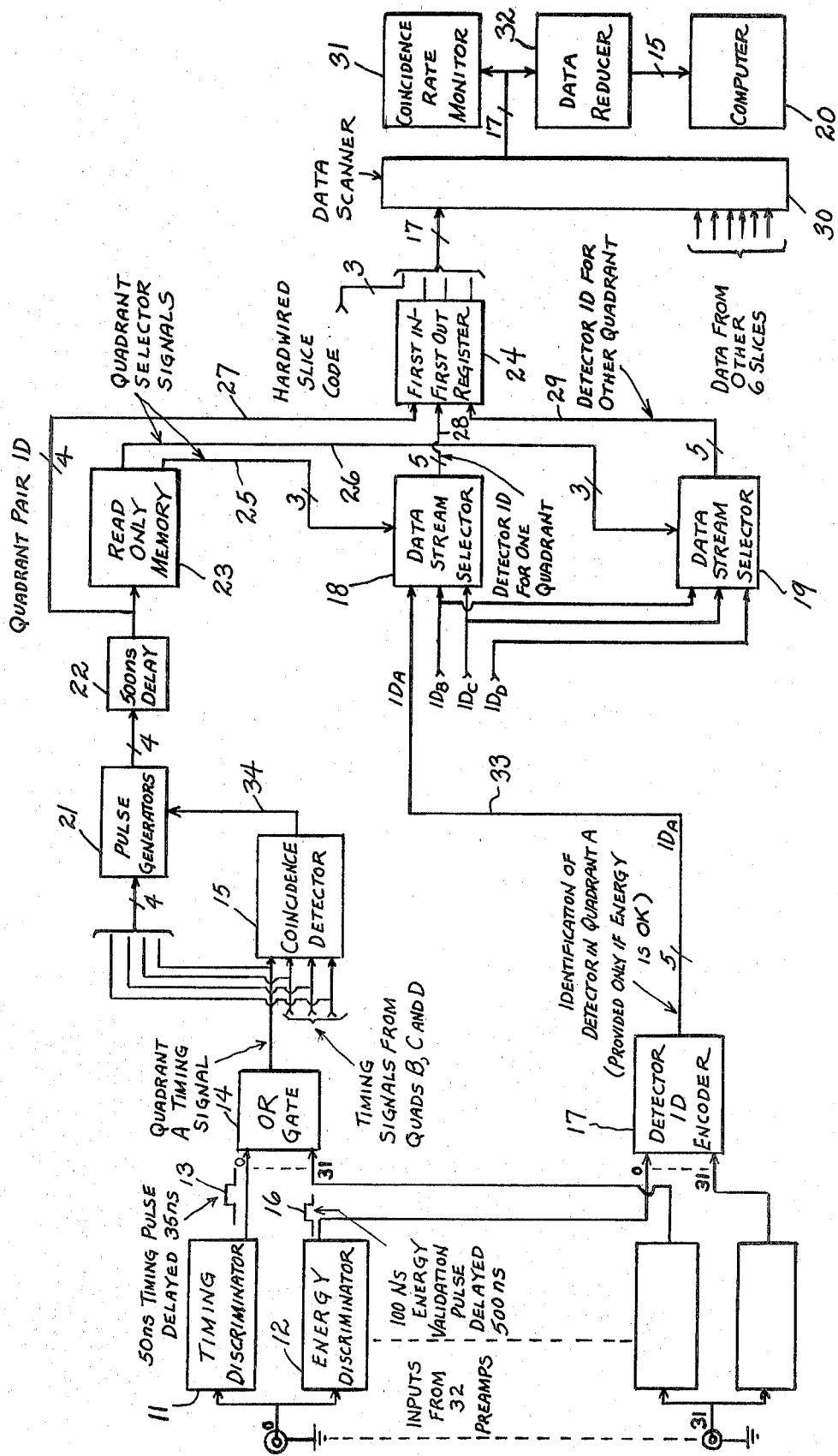
FIG. 1 is a simplified block diagram of the electronic coincidence circuitry associated with one ring of a positron emission tomograph, provided with a coincidence analysis system according to the present invention.

In a typical embodiment of a positron emission tomograph, a scanner is employed which contains four rings, each having 128 detectors, arranged in four quadrants each comprising 32 detectors. Each detector is provided with a fast preamplifier, mounted in the detector assembly, which produces pulses with sharp leading edges. The remainder of the circuitry is mounted in a suitable rack connected to the scanner gantry by 512 coaxial cables that carry the preamplifier outputs to the discriminators. There are two discriminators per channel, as shown in FIG. 1, namely, a timing discriminator circuit 11 and an energy discriminator circuit designated generally at 12. The discriminator circuitry may be similar to that shown in the U.S. patent application of W. S. Friauf et al entitled "Nuclear Pulse Discriminator", Ser. No. 209,305, filed Nov. 21, 1980.

The fast timing discriminator 11 triggers at a very low voltage level corresponding to the first detected photon; this timing signal, shown at 13, is delayed for 35 nsec to ensure that the event is not just noise, and then is passed through a quadrant (32 detector) OR gate circuit 14 (because intraquadrant concidences are not of interest). The timing signals from each quadrant (A, B, C and D) are connected to a four-input coincidence detector 15 with an adjustable coincidence window provided by combinations of 2 nsec gate delays. The coincidence detector 15 may be similar to that disclosed in the U.S. patent application of W. S. Friauf, entitled "Four-Input Coincidence Detector", Ser. No. 222,936, filed Jan. 6, 1981.

The second discriminator 12 in each channel integrates the input pulse for 500 nsec and produces a validating pulse 16 if the pulse height is above a preset threshold. The threshold may also be adjustable so that it can be set high for high count studies. The addresses of energy-valid events within each quadrant are encoded by an array of gates 17 (see FIG. 2) and are fed to two data stream selectors 18 and 19 (see FIG. 3). Whenever a coincidence is detected in the fast circuit, the appropriate quadrants are interrogated after a 500 nsec delay, and, if a valid event is present, the addresses are sent to a computer, shown at 20.

As above mentioned, FIG. 1 illustrates the coincidence analysis system, according to the present invention, for one ring of a tomograph instrument in which detectors (one for each channel) are divided into four groups called "quadrants". In operation, when input timing pulses from any two of the quadrants A, B, C and D are found by the coincidence detector 15 to have occurred within a specified time of each other, information as to the two quadrants is forwarded to a pulse generator circuit 21 (see FIG. 5). However, it is delayed by 500 nsec delay circuitry 22 (see FIG. 6) so as not to be utilized until energy verification of the two quadrants involved in the coincidence has been effected. The energy validation pulses 16 in the two quadrants involved are encoded by the detector identification encoder 17 (see FIG. 2), and the encoded data is accessed by the data stream selectors 18, 19 on the basis of the delayed quadrant information. The number of delay lines needed to delay this information is far less than the number of channels, and the stability requirement is greatly relaxed.

As shown in FIG. 1, the encoded data from encoders 17 is fed to the various quadrant inputs of data stream selectors 18,19 via 5-conductor cables 33.

Thus, the system illustrated in FIG. 1 determines coincidences between any two detectors out of 128, subject to the constraint that the two must be in different quadrants, and information as to which two are involved must be transmitted to the computer 20.

Figure 3:
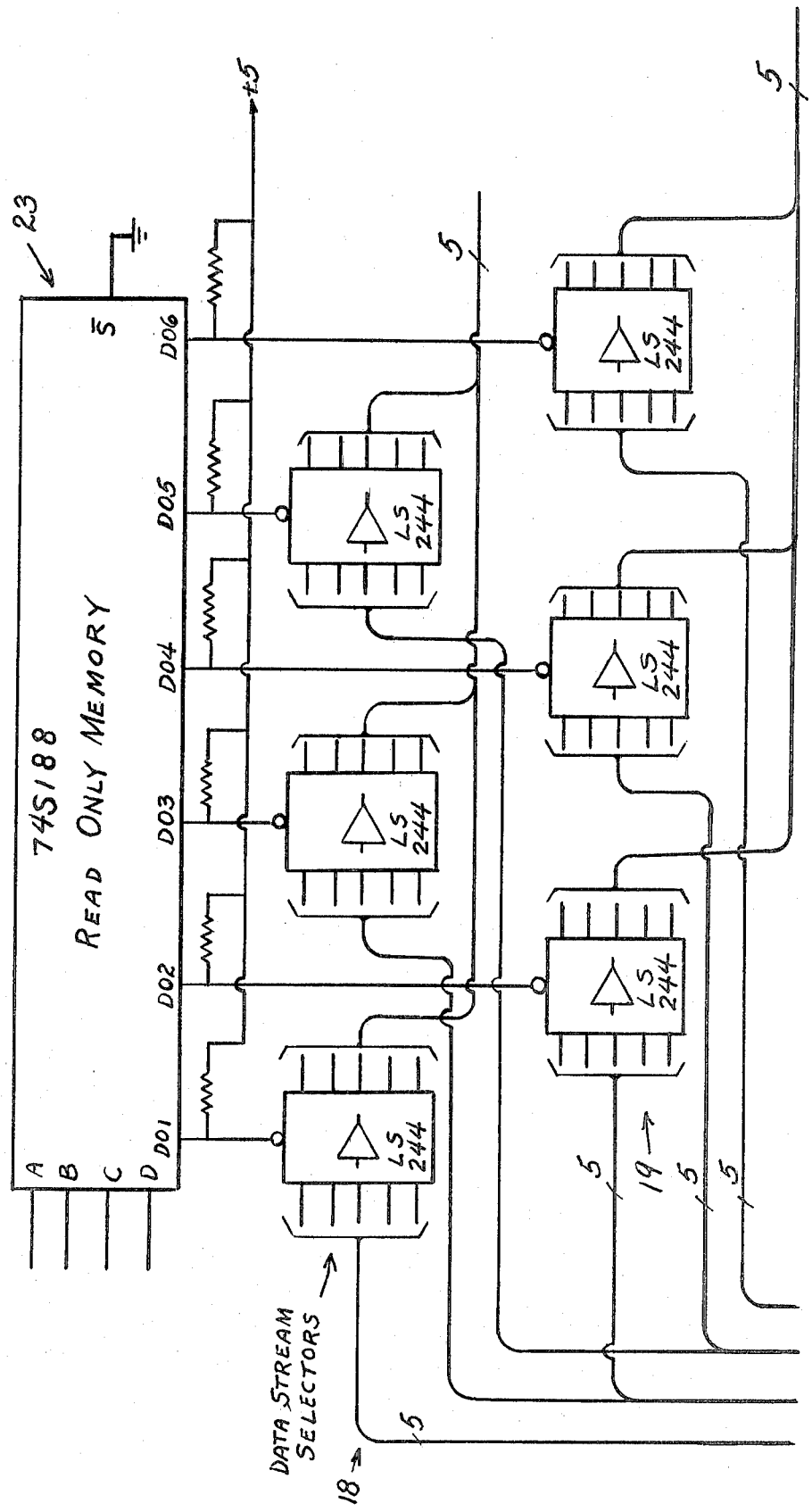
FIG. 3 is a schematic wiring diagram showing a read-only memory and data stream selectors, as employed in the coincidence analysis system of FIG. 1.
Figure 4:
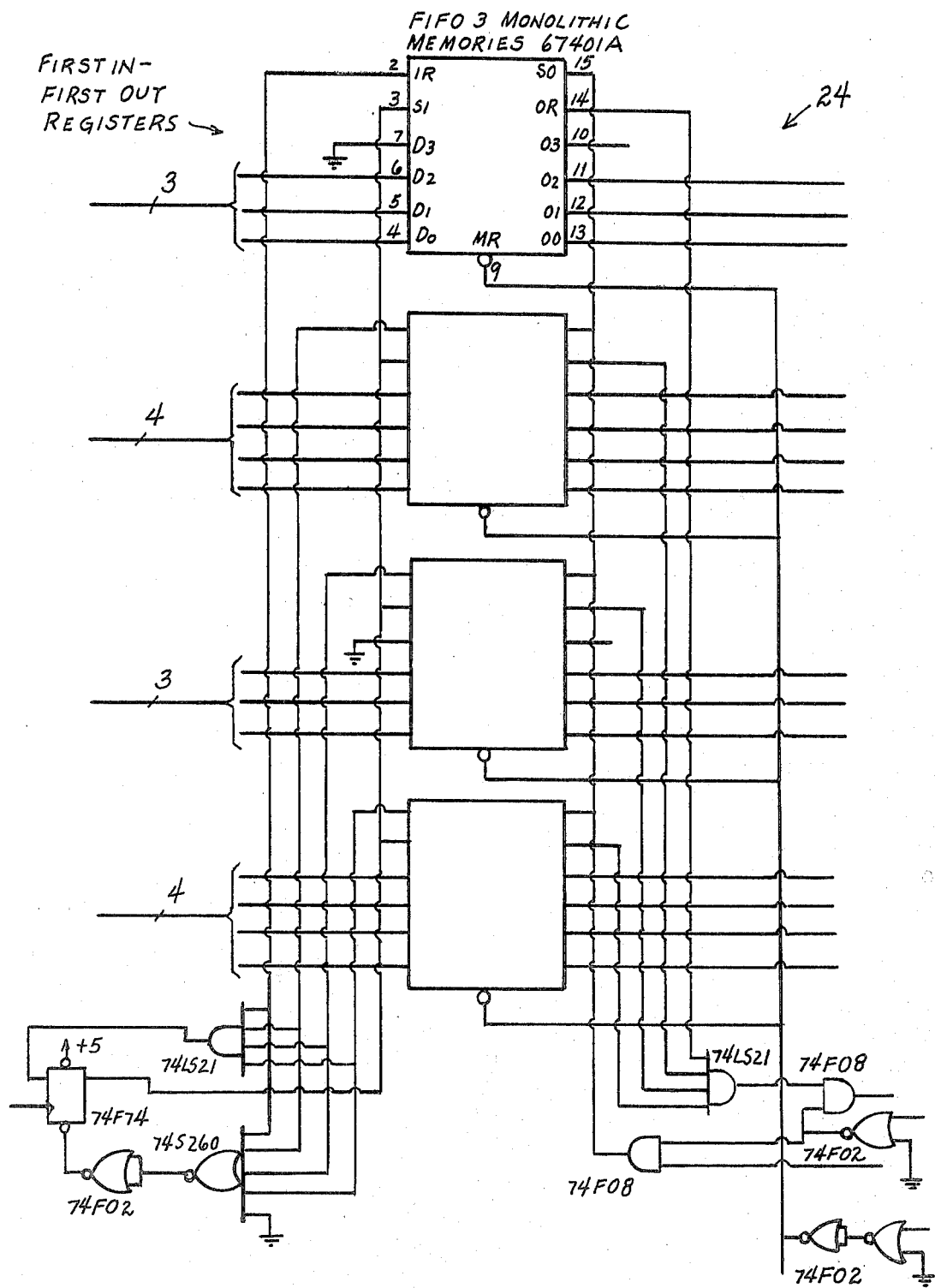
FIG. 4 is a schematic wiring diagram illustrating the first in-first out register circuitry, as employed in the system of FIG. 1.

As shown in FIG. 1, the delayed output pulse from the 500 nsec delay section 22 is fed to a read only memory 23 (see FIG. 3) and is also fed via a 4-conductor cable 27 to a first in-first out register 24 (see FIG. 4).

Also fed to the first in-first out register 24 via 5-conductor cables 28, 29 are the outputs of the data stream selectors 18, 19. The quadrant selector signals from the read only memory 23 are furnished to the data stream selectors 18, 19 via 3-conductor cables 25, 26.

The outputs of first in-first out register 24 are fed to a conventional data scanner 30 with outputs to a coincidence rate monitor 31 and a data reducer 32, which in turn delivers data information to the computer 20.

The four-input coincidence detector 15 has an output line 34, connected as an enabling line for the signal input channels of the pulse generator 21 (see FIG. 5), thereby enabling transmission of the timing pulses 13 responsive to interquadrant signal coincidence.

Figure 2:
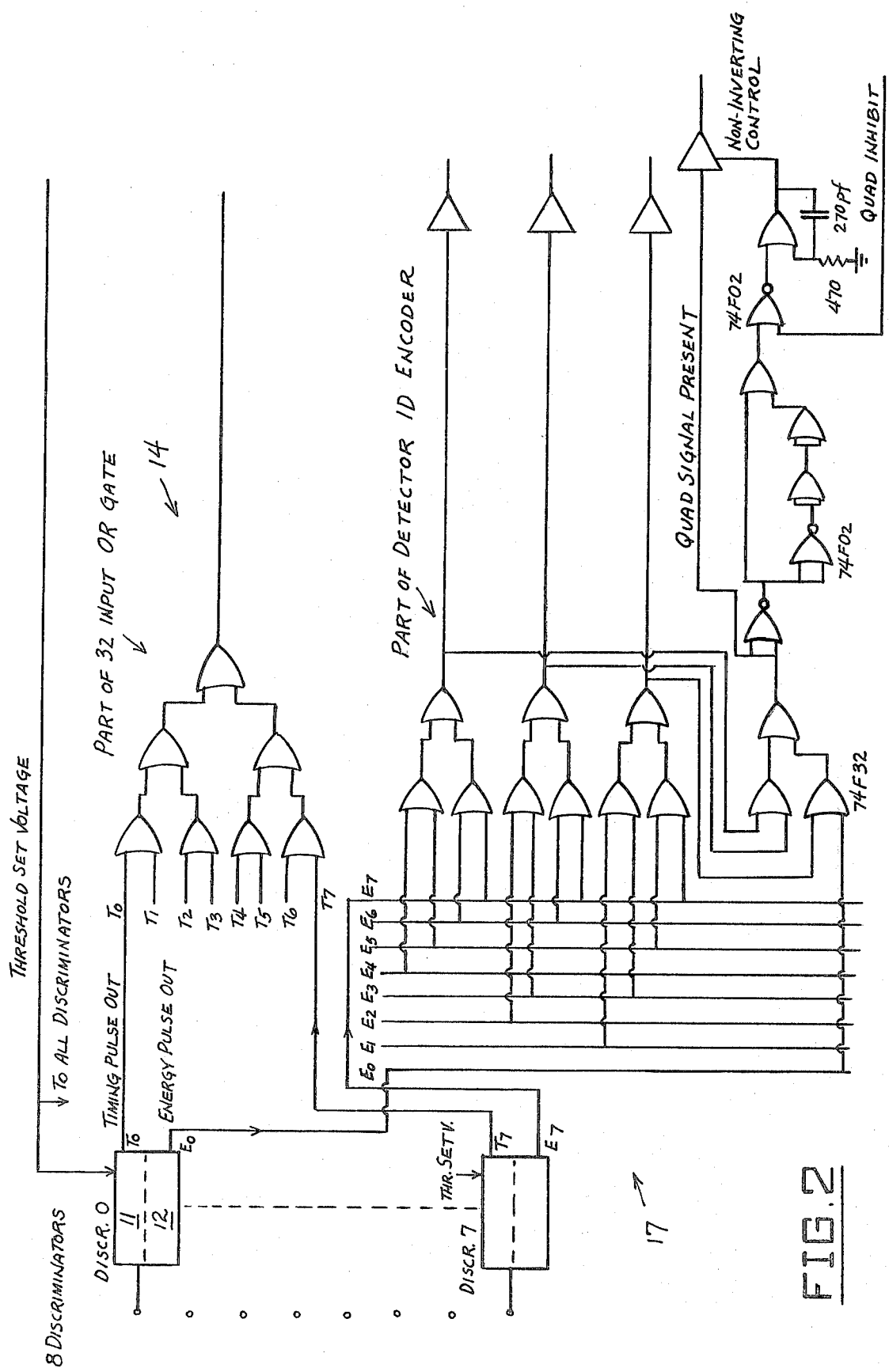
FIG. 2 is a schematic wiring diagram showing part of a 32-input OR gate and part of a detector identification encoder, as employed in the system of FIG. 1.

As will be seen from FIG. 2, the detector identification encoder 17 is a substantially conventional assembly of gates interconnected so that an input on any one of 32 input terminals generates a 5-bit binary coded output that identifies the input.

The data stream selectors 18 and 19, shown in FIG. 3, are conventional devices, which could also be called "digital multiplexers", each of which selects an identification code from the desired quadrant and transmits the code on a common set of output lines.

Figure 5:
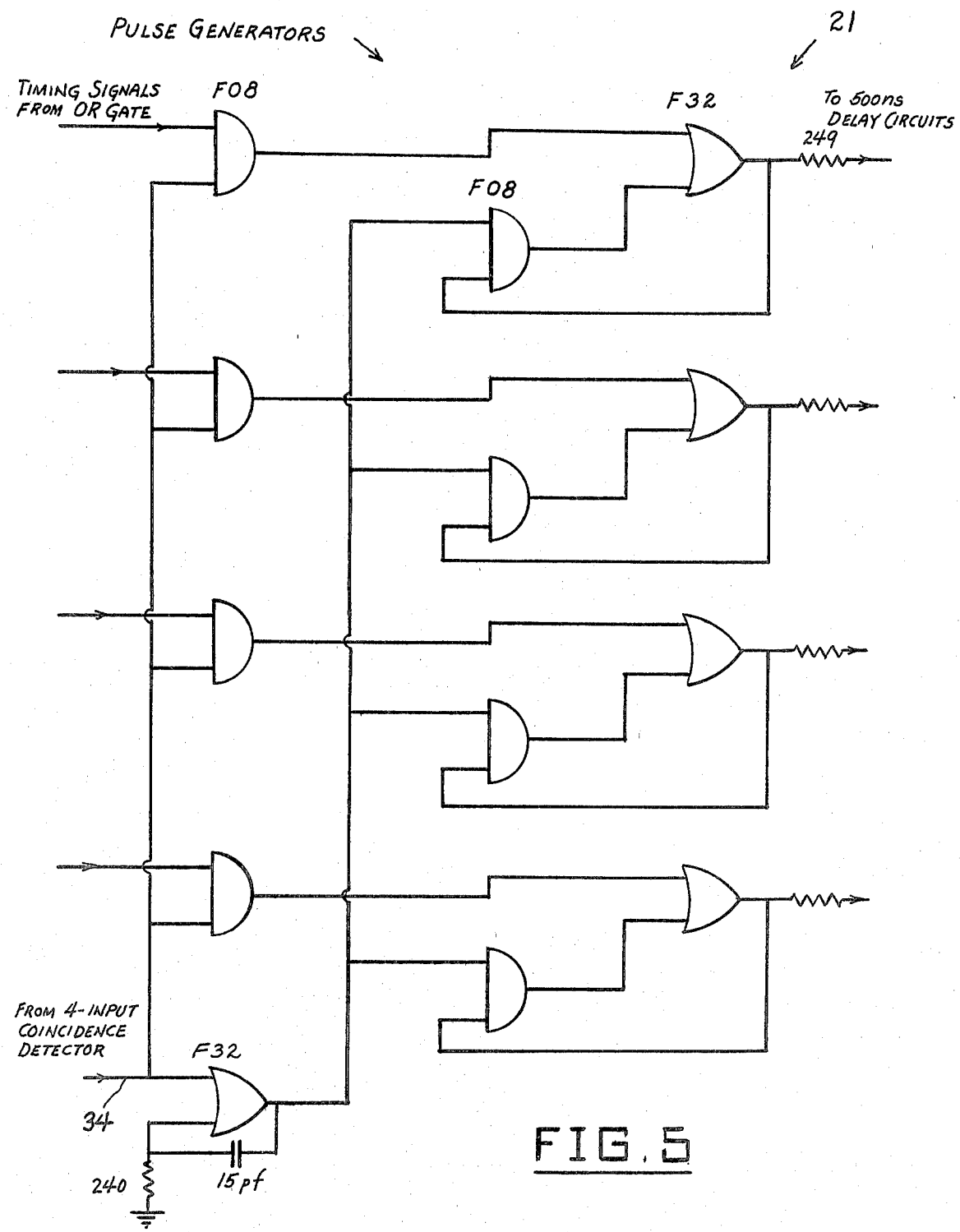
FIG. 5 is a schematic wiring diagram of the pulse generator circuitry employed in the coincidence analysis system of FIG. 1.

The pulse generators 21 of FIG. 5 comprises respective conventional generator devices, each of which generates a digital pulse of approximately 70 nsec duration upon receipt of a digital signal from the coincidence detector 15, signifying that a coincidence has occurred, and also a signal from a quadrant OR gate indicating that this quadrant was involved in the coincidence.

Figure 6:
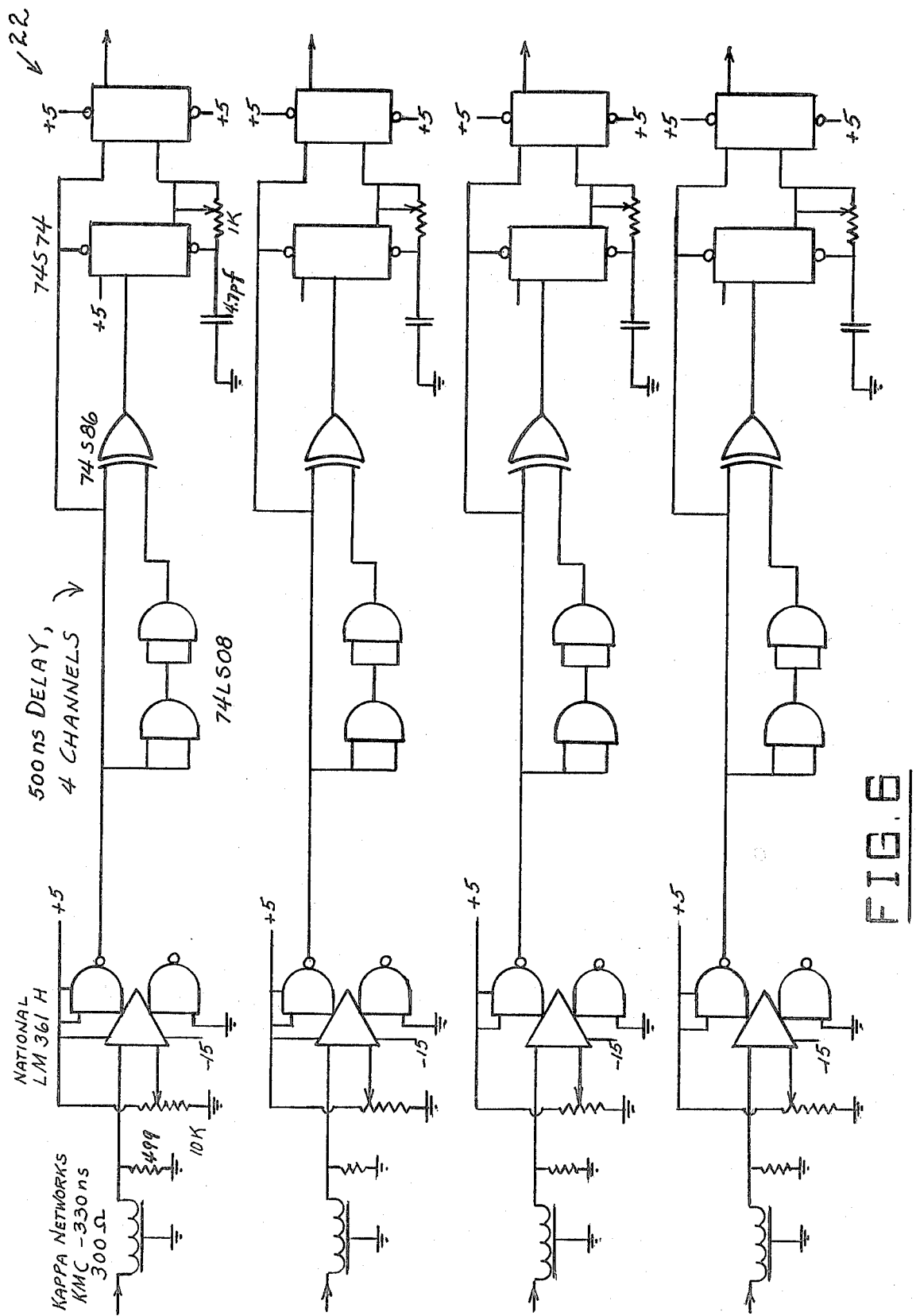
FIG. 6 is a schematic wiring diagram of the 500 ns delay circuitry employed in the system of FIG. 1.

The 500 nsec delay assembly 22 shown in FIG. 6 comprises conventional delay lines and associated components that delay pulses by approximately 500 nsec.

The read only memory 23 shown in FIG. 3 is a conventional semi-conductor device which is preprogrammed to provide desired output codes on a set of output lines in response to input codes on a set of input lines. The input codes can be regarded as memory location addresses, and the output codes as the contents of those addresses.

The first in-first out register 24 of FIG. 4 is a conventional shift register in which inputs and outputs can occur asynchronously, the first data read in being the first to come out. A considerable number of data points can be entered before any are read out, without any loss of data.

While a specific embodiment of an improved gamma ray coincidence analysis system has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. A coincidence analysis system for a multichannel nuclear emission tomograph of the type employing scintillation detectors arranged in a plurality of groups, each said group comprising a plurality of spaced respective detectors defining scintillation detector channels, each of said detector channels producing output pulses having sharp leading edges, respective discriminator means associated with each of said channels, means for connecting the detectors to the respective discriminator means, said discriminator means being each provided with means generating a timing pulse and an energy verification pulse delayed by a predetermined validation period relative to said timing pulse, each said timing pulse being produced in response to each said sharp leading edge of a detector pulse, coincidence detector means to generate a resultant coincidence signal responsive to the coincidence of timing pulses from the detector channels of any two of the groups, means to delay said resultant coincidence signal for a time substantially equal to said energy validation period, and means to generate a data output signal responsive to the concurrence of the delayed resultant coincidence signal and the delayed energy verification pulses.

2. The coincidence analysis system of claim 1, and wherein the coincidence detector means comprises a multiple-input coincidence detector with inputs corresponding to the number of groups of scintillation detectors.

3. The coincidence analysis system of claim 1, and means to generate an identification coding signal from the delayed energy verification pulse, and wherein said means to generate the data output signal includes means responsive to the concurrence of the delayed resultant coincidence signal and the identification coding signals.

4. The coincidence analysis system of claim 1, and wherein the energy validation period is approximately 500 nsec.

5. The coincidence analysis system of claim 1, and wherein said timing pulse is approximately 50 nsec in length.

6. The coincidence analysis system of claim 5, and wherein the energy verification pulse is approximately 100 nsec in length.

7. The coincidence analysis system of claim 1, and wherein each group of scintillation detectors comprises a quadrant containing 32 detectors.

8. The coincidence analysis system of claim 7, and wherein the coincidence detector means comprises a four-input coincidence detector with inputs from four respective quadrants.

9. The coincidence analysis system of claim 8, and wherein said coincidence detector means includes OR gate means arranged to transmit the timing pulses from the discriminator means associated with the respective quadrants to the inputs of the four-input coincidence detector.

10. A method of coincidence analysis for multi-channel nuclear emission topography which employs a ring-like array of scintillation detectors arranged in groups, each said detector producing timing pulses having sharp leading edges, comprising generating timing signals and energy signals responsive to substantially concurrent scintillations detected in two different groups, said timing signals being produced in response to said sharp leading edges of said detector pulses, delaying the energy signal for a predetermined energy validation period, generating a coincidence signal responsive to the coincidence of two timing signals from said two different groups, thereafter delaying said coincidence signal for a period substantially the same as said energy validation period, and forming an output data signal responsive to the concurrence of said delayed coincidence signal and said delayed energy signals.

11. The method of claim 10, and employing an energy validation signal delay of approximately 500 nsec.

12. The method of claim 11, and employing a timing signal in the form of a pulse with a duration of approximately 50 nsec and an energy signal in the form of a pulse with a duration of approximately 100 nsec.

* * * * *